(12) United States Patent
Stefanovic

(10) Patent No.: US 8,729,090 B1
(45) Date of Patent: May 20, 2014

(54) COMPOSITIONS AND METHODS FOR INHIBITING COLLAGEN PRODUCTION

(71) Applicant: Florida State University Research Foundation, Inc., Tallahassee, FL (US)

(72) Inventor: Branko Stefanovic, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 13/646,001

(22) Filed: Oct. 5, 2012

Related U.S. Application Data

(60) Provisional application No. 61/543,370, filed on Oct. 5, 2011.

(51) Int. Cl.
*A61K 31/519* (2006.01)
*C07D 471/14* (2006.01)

(52) U.S. Cl.
USPC .......................................... 514/267; 544/250

(58) Field of Classification Search
USPC .................................. 514/267; 544/250, 252
See application file for complete search history.

(56) References Cited

U.S. PATENT DOCUMENTS

2005/0002917 A1    1/2005   Schwartz et al.

OTHER PUBLICATIONS

Iannou (PubChem Assay AID#485297, Deposit date Sep. 29, 2010).*
Nemoto et al ("Different transcriptional mechanisms control collagen gene expression in a hepatoma cell line and mesenchymal cells." International Hepatology Communications, 1995; 3(Suppl):60-60(1).*
Vincent et al ("Evaluation of an Anti-Tumor Necrosis Factor Therapeutic in a Mouse Model of Niemann-Pick C Liver Disease" PLoS One 2010; 5(9):e12941).*
Kisseleva et al ("Role of hepatic stellate cells in fibrogenesis and the reversal of fibrosis." Journal of Gastroenterology and Hepatology 2007; 22(Suppl. 1): S73-S78).*
Williams et al ("Drug Design and Relationship of Functional Groups to Pharmacological Activity"; David A Williams and Thomas L Lemke; Foye's Principles of Medicinal Chemistry, 5th Edition, 2002; 37-67).*
Cai et al., Binding of LARP6 to the Conserved 5' Stem-Loop Regulate Translation of mRNAs Encoding Type I Collgagen, Journal of Molecular Biology, (2010), 395, 309-326.

* cited by examiner

*Primary Examiner* — Timothy Thomas
*Assistant Examiner* — Rayna B Rodriguez
(74) *Attorney, Agent, or Firm* — Dyer Allen et al.

(57) ABSTRACT

Embodiments of the invention include compositions effective for inhibiting collagen production and related methods. A preferred method comprises contacting at least one cell capable of producing collagen with a composition effective for inhibiting collagen production thereby. The composition comprises one or more of the compounds effective for inhibiting collagen production disclosed herein.

6 Claims, 3 Drawing Sheets

COMPOSITIONS AND METHODS FOR INHIBITING COLLAGEN PRODUCTION

CROSS-REFERENCE TO RELATED APPLICATIONS

Priority is claimed to provisional application Ser. No. 61/543,370 filed Oct. 5, 2011, which is titled "Compositions and Related Methods for Targeting Synthesis of Type I Collagen" and is incorporated by reference in its entirety.

FIELD OF THE INVENTION

This invention relates to the field of antifibrotics. More particularly, the invention relates to antifibrotics that function by inhibiting collagen production.

BACKGROUND

Fibrosis is characterized by the excessive synthesis of an extracellular matrix composed of Type 1 collagen. It affects the liver, lungs, heart, intestines, kidneys, skin, joints and adventitia of blood vessels. Fibrosis has been shown to affect 45% of the population.

In my previous work, which is presented in co-pending U.S. application Ser. No. 12/898,849, I showed that the interaction between the LARP6 protein and the 5' stem loop in collagen α1(I) and collagen α2(I) mRNAs is important for the excessive expression of type 1 collagen in fibrosis. I also showed that the compound ML-7, which is shown below, interferes with collagen synthesis.

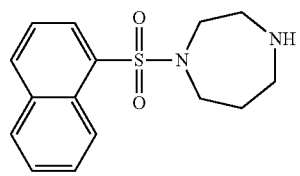

ML-7

SUMMARY

I have now discovered that other compounds are also inhibit collagen production. Accordingly, embodiments of the invention provide compositions and methods for inhibiting collagen production. In a method aspect of the invention, a method of inhibiting collagen production comprises contacting cells capable of producing collagen with one or more of the compositions.

Moreover, at least two of the compounds effective for inhibiting collagen production are effective to do so at nanomolar concentrations. These methods and compounds are especially useful at combating fibrosis in various cell types.

These and other aspects, embodiments, and features of the invention will be better understood in the context of the accompanying drawings and the following Detailed Description of Preferred Embodiments.

DETAILED DESCRIPTION OF PREFERRED EMBODIMENTS

Figure 1:
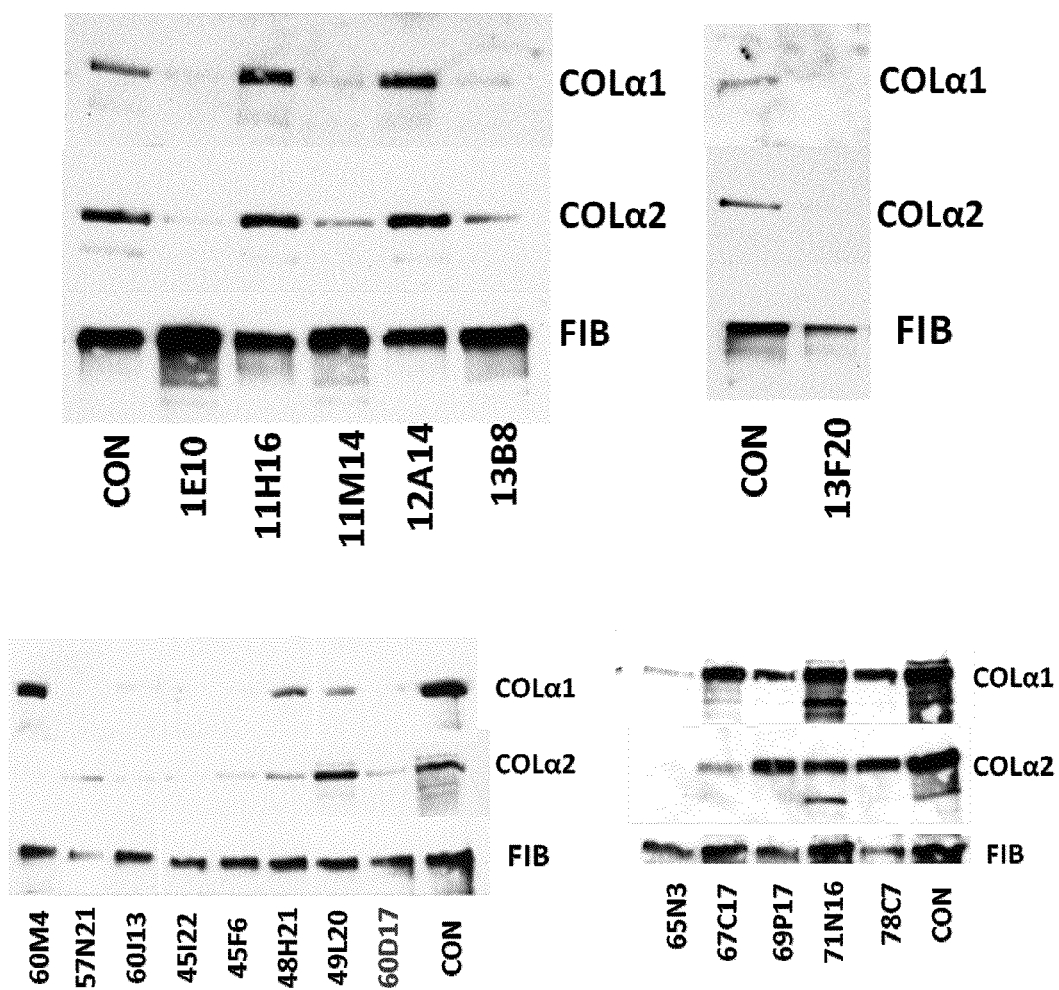
FIG. 1 is western blot data for human lung fibroblasts treated with some of the effective compounds, in accordance with an aspect of the invention.

In the Summary above and in the Detailed Description of Preferred Embodiments, reference is made to particular features (including method steps) of the invention. Where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features, ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will convey preferred embodiments of the invention to those skilled in the art.

In an embodiment of the invention, a method of inhibiting collagen production involves contacting at least one cell capable of producing collagen with a compound effective for inhibiting collagen production thereby. Cells capable of producing collagen include, but are not limited to fibroblasts and hepatic stellate cells.

The term "contacting" refers to placing the compound in direct physical association with the collagen producing cell. Contacting can be achieved using either a solid, liquid, or gaseous form of the effective compound. It includes events that take place both intracellularly and extracellularly. Contacting may also be accomplished by a conventional pharmaceutical administration technique that one would use on a patient. Suitable administration techniques include administering one or more pharmaceutically acceptable dosage forms such as suspensions, tablets, suppositories, capsules, injectables, transdermals or the like. Other suitable administration techniques include oral, sublingual, buccal, intravenous, subcutaneous, transcutaneous, intramuscular, intracutaneous, intrathecal, epidural, intraocular, intracranial, inhalation, itraperitoneal, or the like. Any combination of these administration techniques may also be used.

According to a composition aspect of the invention, the effective compound is an active ingredient in a pharmaceutical composition. In such embodiments, the effective compound is blended with one or more excipients useful for making the composition into a pharmaceutically acceptable dosage form such as a suspension, tablet, capsule, injectable, or the like that can be administered to a human or animal patient. Exemplary excipients include one or more diluents, disintegrants, emulsifiers, solvents, processing aids, buffering agents, colorants, flavorings, solvents, coating agents, binders, carriers, glidants, lubricants, granulating agents, gelling agents, polishing agents, suspending agent, sweetening agent, anti-adherents, preservatives, emulsifiers, antioxidants, plasticizers, surfactants, viscosity agents, enteric agents, wetting agents, thickening agents, stabilizing agents, solubilizing agents, bioadhesives, film forming agents, emollients, dissolution enhancers, dispersing agents, or combinations thereof.

Preferred effective compounds that are used in accordance with embodiments of the invention are now described with reference to Tables 1-4. In Tables 1-4, each compound is identified according to its molecular structure. The structures provided are intended to generally illustrate the structure of the molecule and are not intended to be limited to thereto. Instead, the structures are provided to show where the general constituents are located on each molecule. For example, the structures are not intended to be limited to the particular stereoisomer shown. The compounds should be understood to include all of the stereoisomers that occur with a given structure.

Some of the compounds provided in Tables 1-4 include R groups. "R," "$R_1$", "$R_2$," and "$R_3$" represent functional groups, which are typically, but not necessarily, organic. They are preferably selected from alkyl, ketone, phenyl, aldehyde, amine, carboxylic, ether, ester, amine, alcohol, carbonyl, amide, alkyl halide, anhydride, nitride, alkoxy, thio, nitrile, hydrogen, and halide groups. Alternatively, they may be composed of a more complex structure in which one or more of these individual functional groups are bound together to form a composite functional group. Where a particular R group is shown, the dotted line represents the preferred position at which the R group is bound to the parent compound.

A first class of compounds effective for inhibiting collagen production has the general formula shown in Compound 1 (Table 1). In particularly preferred embodiments of Compound 1, R is Compound 1—R Group A, Compound 1—R Group B or Compound 1—R Group C. In Compound 1—R Group A, $R_1$ and $R_2$ may be selected either together or individually from any of the previously described R groups, among others.

A second class of compounds effective for inhibiting collagen production has the general formula shown in Compound 2 (Table 2). In particularly preferred embodiments of Compound 2, R is Compound 2—R Group A, or Compound 2—R Group B.

A third class of compounds effective for inhibiting collagen production has the general formula shown in Compound 3 (Table 3). In particularly preferred embodiments of Compound 3, R is Compound 3—R Group A, Compound 3—R Group B, Compound 3—R Group C, Compound 3—R Group D, Compound 3—R Group E, or Compound 3—R Group F. $R_1$, $R_2$, and $R_3$ may be selected either together or individually from any of the previously described R groups, among others.

In even more particular embodiments of the invention, the effective compound is selected from one or more of the compounds listed in Table 4.

The effective compounds are made according to conventional synthetic techniques. The compounds listed in Table 4 are commercially available from ChemBridge Corporation of San Diego, Calif.

EXAMPLES

The embodiments of the invention described above will be even better understood in the context of the following examples. These examples are not intended to limit the scope of the invention in any way.

Example 1

Inhibition of Collagen Production by Human Lung Fibroblasts

This section shows that the effective compounds inhibit human lung fibroblasts from synthesizing collagen.

Several chemical compounds were identified in this screen and tested for their ability to inhibit collagen production by primary human lung fibroblasts in culture. Lung fibroblasts are responsible for development of lung fibrosis. The compounds were added in a single dose of 100 µM to the lung fibroblasts, except compound 60D17, which was added at 10 µM. Two days after the addition of the compounds, the secretion of type I collagen into the cellular medium was analyzed by western blot. Both polypeptides which form type I collagen, COLα1(I) and COLα2(I), were analyzed.

FIG. 1 shows the effect of several of the effective compounds on collagen production by human lung fibroblasts. Here, COLα1 represents the α1 polypeptide of type I collagen, COLα2 represents the α2 polypeptide of type I collagen, and FIB represents fibronectin, which was the control. These results indicate that the compounds 1E10, 13F20, 60J13, 45I22, 45F6, 60D17, 65N3, 11M14, 13B8, 57N21, 49L20, 60M4 and 67C17 posses antifibrotic activity. These compounds can be chemically modified to increase their potency and may represent valuable chemical scaffolds that can be modified to produce even more potent antifibrotic drugs It is clear from FIG. 1 that compounds 1E10, 13F20, 60J13, 45I22, 45F6, 60D17 and 65N3 dramatically reduced excretion of both collagen polypeptides. Compounds 11M14, 13B8, 57N21 and 49L20 reduced production of α1(I) polypeptide more than that of α2 polypeptide, while compounds 60M4 and 67C17 reduced α2 polypeptide more than α1 polypeptide. Since type I collagen can be formed only if both polypeptides are made, these compounds are equally as effective as the compounds that inhibit production of both polypeptides. Secretion of fibronectin, another extracellular matrix protein, was not affected by any of the compounds, suggesting that the compounds affected type I collagen specifically.

Example 2

Inhibition of Collagen Production by Hepatic Stellate Cells (HSCs)

This section shows that the effective compound 60D17 inhibits collagen synthesis by HSCs.

HSCs are liver cells responsible for collagen synthesis in hepatic fibrosis. In normal liver these cells store vitamin A, but do not express type I collagen. In fibrotic livers, HSCs increase type I collagen expression 50-100 fold. Similar changes can be reproduced when HSCs are isolated from rat livers and cultured in vitro.

Three days after isolation and culturing, the HSCs still retain their quiescent phenotype and show little collagen expression. At day 5 after isolation the first significant increase in collagen expression becomes evident. After 7-8 days of culturing type I collagen expression increases 50-100 fold and attains its maximal level.

I used this model to test the efficacy of 60D17 in inhibiting collagen expression, because it is relevant to liver fibrosis. 60D17 was added at 100 nM and 250 nM concentrations to HSCs at day 3 in the culture. The cells were cultured until day 7 and the level of collagen α1(I) polypeptide was measured by western blot.

Figure 2:
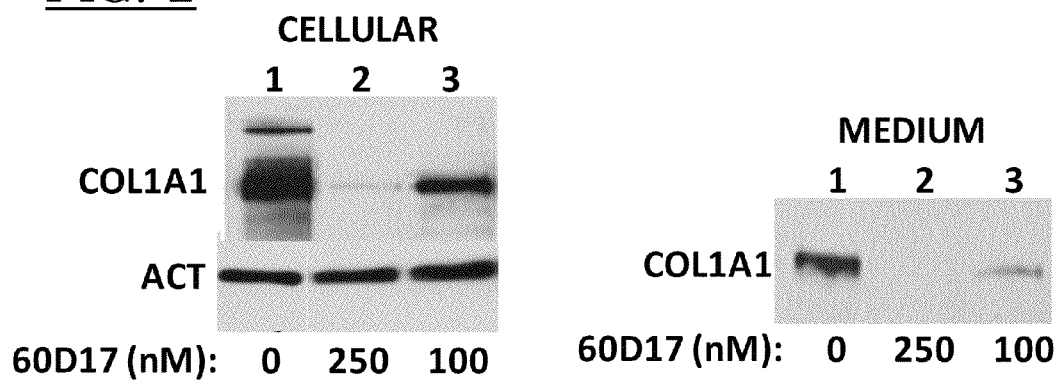
FIG. 2 is western blot data showing that compound 60D17 inhibits collagen production by hepatic stellate cells (HSCs), in accordance with an aspect of the invention.

FIG. 2 shows the data corresponding to inhibition of collagen α1(I) polypeptide synthesis by 60D17 in HSCs subjected to fibrogenic activation in vitro. Lane 1 contained untreated cells. Lane 2 contained HSCs treated with 250 nM of 60D17. Lane 3 contained HSCs treated with 100 nM of 60D17. The panel on the left represents the cellular levels of collagen α1(I) polypeptide measured by western blot. Actin (ACT) was used as the loading control. The right panel represents the collagen α1(I) polypeptide level in the cellular medium.

As FIG. 2 shows, 250 nM of 60D17 almost completely blocked the increase in collagen expression that normally takes place during culturing of isolated HSCs (compare lane 1 and lane 2). 100 nM of 60D17 was less potent, but still significantly inhibited collagen production by HSCs (lane 3). These results indicate that the 60D17 compound is highly effective at nanomolar concentrations in inhibiting type I collage production by HSCs.

Example 3

Inhibition of Collagen Production by Rat Liver Cells

This example shows that the effective compound 60D17 inhibits collagen production by rat liver cells.

Figure 3:
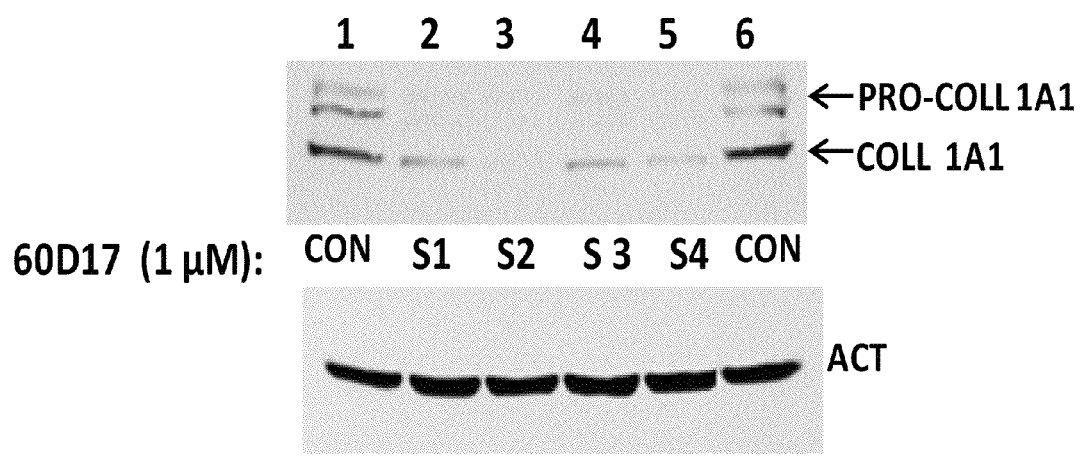
FIG. 3 is western blot data showing the effect of compound 60D17 on collagen expression in liver slices, in accordance with an aspect of the invention.

FIG. 3 shows the effect of 60D17 on collagen expression in rat liver slices. In these experiments 60D17 was added to four different slices (lanes 2-5) for days at 1 μM concentration. The expression of both collagen α1(I) polypeptide, resolved here as procollagen (PRO-COLL1A1), and processed mature collagen (COLL 1A1) were measured by western blot. Lanes 1 and 6 were untreated control. Actin (ACT) was used as the loading control.

Precision cut liver slices were prepared from rat liver with a thickness of 350 μm and diameter of 8 mm. These slices were cultured in vitro for several days. Cutting the liver represents an injury thereto. In response to this injury, the slices initiate profibrotic changes. The response is similar to the fibrotic response of the intact organ, because the slices retain all different cell types and proper architecture of the organ. Thus, they mimic fibrosis initiation of the whole liver. Accordingly, this is a useful model to test the efficacy of 60D17 in blocking the profibrotic reaction.

As can be seen in FIG. 3, the addition of 60D17 to four different slices (S1-S4) for 4 days at concentration of 1 μM significantly inhibited expression of collagen α1(I) polypeptide in all 4 slices (lanes 2-5), as compared to two untreated slices which showed strong profibrotic reaction (lanes 1 and 6). This indicated that 60D17 has the ability to prevent profibrotic reactions in the liver organ culture and that it is highly likely that it will be also effective in animal models of liver fibrosis. Initial animal studies have shown that the compound is well tolerated by rats.

Example 4

Inhibition of Collagen Production by 60D17 in Lung Fibroblasts in Theraputic Concentrations This example shows the effective compound 60D17 inhibits collagen synthesis by lung fibroblasts at different concentrations.

Figure 4:
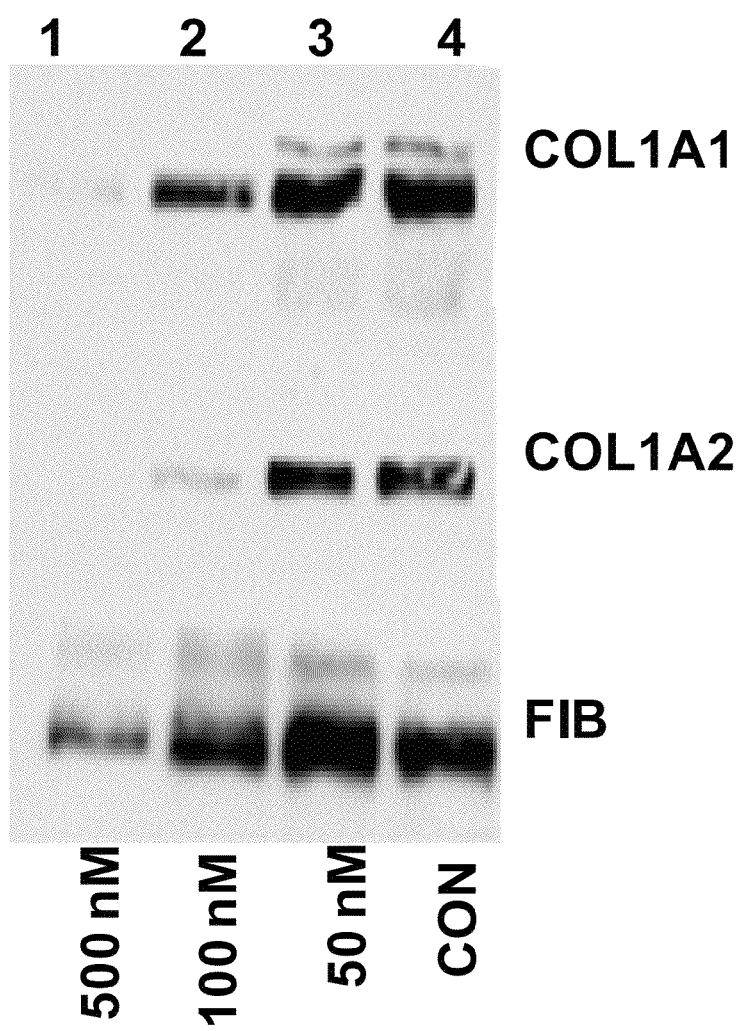
FIG. 4 is western blot data showing the effect of compound 60D17 on the type 1 collagen expression of lung fibroblasts at different concentrations, in accordance with an aspect of the invention.

FIG. 4 shows the effect of 60D17 on type I collagen expression of lung fibroblasts in therapeutic concentrations. In lung fibrosis the process of excessive collagen accumulation is similar to the liver, but the cells responsible for collagen synthesis are lung fibroblasts. Therefore, I tested the potency of 60D17 at therapeutic concentrations in lung fibroblasts before 60D17 was tested at higher concentrations in these cells.

As shown in FIG. 4, treatment of lung fibroblasts with 500 nM of 60D17 for 18 h almost completely inhibited the ability of these cells to produce both polypeptides comprising type I collagen (lane 1). At 100 nM 60D17 dramatically inhibited synthesis of collagen α2(I) polypeptide and had smaller effect on α1(I) polypeptide (lane 2). It was substantially ineffective at 50 nM. Lane 4 represents untreated control cells. These results indicate that 60D17 is equally potent in lung fibroblasts as it is in HSCs and that, because of its effectiveness at nM concentrations, it has promising utility as an antifibrotic drug compound.

A derivative of 60D17, 60D17-G also showed promising results. It also interfered with the synthesis of type I collagen at nM concentrations.

The invention has been described above with reference to the accompanying drawings, in which preferred embodiments of the invention are shown. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

In the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and as defined in the appended claims.

TABLE 1

| Compound 1 and Related R Groups | |
|---|---|
| Name | Diagram |
| Compound 1 | O, N—R (six-membered ring) |
| Compound 1-R Group A | $R_2$, $R_1$ (phenyl ring) |

TABLE 1-continued

Compound 1 and Related R Groups

| Name | Diagram |
|---|---|
| Compound 1-R Group B | (structure: N-(5-methoxyphenyl)pivalamide) |
| Compound 1-R Group C | (structure: 4-(methylsulfonyl)-N-((1-ethylpyrrolidin-2-yl)methyl)benzamide) |

TABLE 2

Compound 2 and Related R Groups

| Name | Diagram |
|---|---|
| Compound 2 | (structure: 2-substituted naphthalene with R group) |
| Compound 2-R Group A | (structure: pyrazolo[3,4-b]pyridinone with dimethylpyrimidine) |
| Compound 2-R Group B | (structure: 4,6-dimethylpyrimidin-2-yl linked to 5-hydroxypyrazole) |

TABLE 3

Compound 3 and Related R Groups

| Name | Diagram |
|---|---|
| Compound 3 | (structure: pyrrolo-pyrimido-pyridine core with $R_1$, $R_2$, $R_3$ substituents) |
| Compound 3-R Group A | H |
| Compound 3-R Group B | (structure: 1-phenylpiperidine) |
| Compound 3-R Group C | (structure: methyl ester -CH₂C(O)OCH₃) |
| Compound 3-R Group D | (structure: 3-pyridyl) |
| Compound 3-R Group E | (structure: phenyl) |
| Compound 3-R Group F | $CH_3$ |

TABLE 4

Other Compounds that Inhibit Collagen Production

| Name | Diagram |
|---|---|
| 1E10 | (structure: 4-morpholinophenyl methylamine) |
| 45I22 | (structure: N-(2-morpholino-5-methoxyphenyl)pivalamide) |
| 57N21 | (structure: 4-(morpholinosulfonyl)-N-((1-ethylpyrrolidin-2-yl)methyl)benzamide) |

TABLE 4-continued

Other Compounds that Inhibit Collagen Production

| Name | Diagram |
|---|---|
| 13B8 | 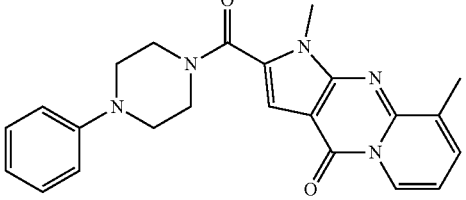 |
| 60J13 | 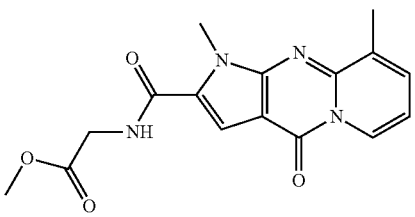 [SMILES: COC(=O)CNC(=O)c1cc2c(=O)n3cccc(C)c3nc2n1C] |
| 60D17 | 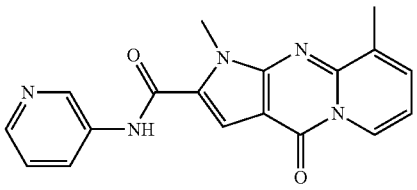 [SMILES: Cc1cccn2c(=O)c3cc(C(=O)Nc4cccnc4)n(C)c3nc12] |
| 60D17-G | 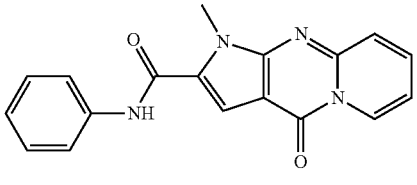 [SMILES: Cn1c(C(=O)Nc2ccccc2)cc2c(=O)n3ccccc3nc21] |
| 13F20 | 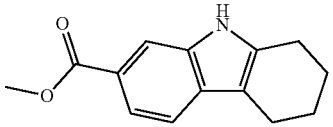 [SMILES: COC(=O)c1ccc2c3c([nH]c2c1)CCCC3] |
| 45F6 | 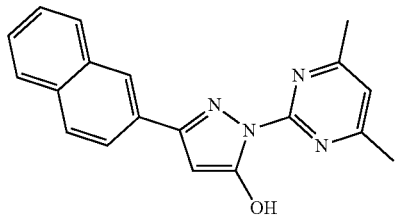 [SMILES: Cc1cc(C)nc(-n2nc(-c3ccc4ccccc4c3)cc2O)n1] |
| 49L20 | 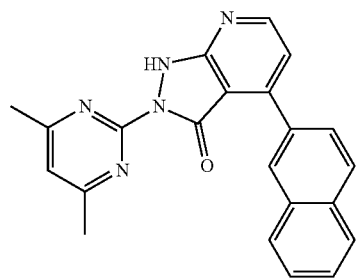 [SMILES: Cc1cc(C)nc(-n2[nH]c3nccc(-c4ccc5ccccc5c4)c3c2=O)n1] |
| 11M14 | 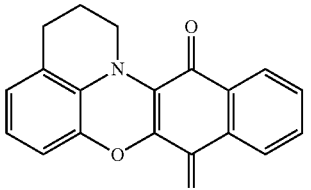 |
| 67C17 | 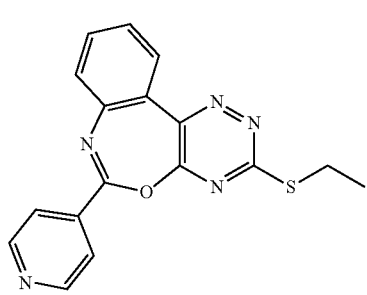 [SMILES: CCSc1nnc2c(n1)OC(c1ccncc1)=Nc1ccccc1-2] |
| 60M4 | 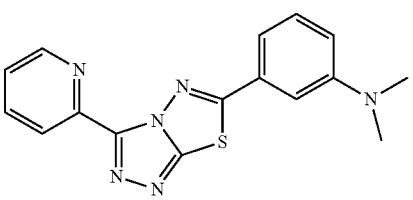 [SMILES: CN(C)c1cccc(-c2nn3c(-c4ccccn4)nnc3s2)c1] |
| 65N3 | 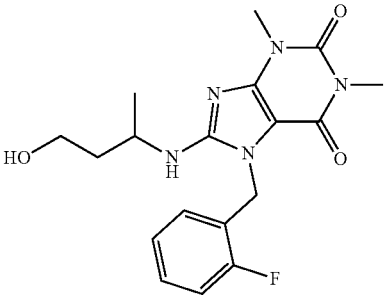 [SMILES: CC(CCO)Nc1nc2c(c(=O)n(C)c(=O)n2C)n1Cc1ccccc1F] |

What is claimed is:

1. A method of inhibiting collagen production, the method comprising contacting at least one cell capable of producing collagen with a composition effective for inhibiting production thereby, the composition comprising one or more compounds having the structure

wherein R1 and R2 together form the structure

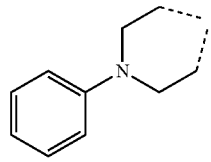

or R1 or R2 is selected from the group consisting of

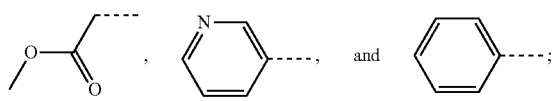

the other of R1 or R2 is H; and R3 is an alkyl group or H.

2. The method of claim 1, wherein the composition comprises

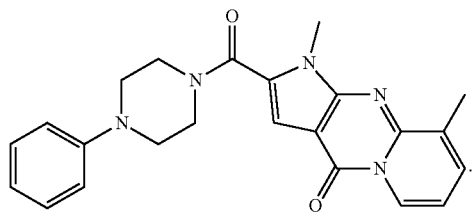 [SMILES: Cc1cccn2c(=O)c3cc(C(=O)N4CCN(c5ccccc5)CC4)n(C)c3nc12]

3. The method of claim 1, wherein the composition comprises

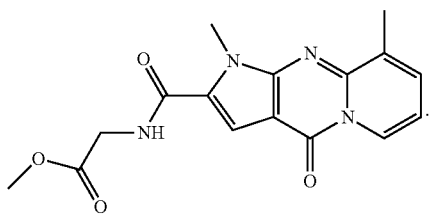 [SMILES: COC(=O)CNC(=O)c1cc2c(=O)n3cccc(C)c3nc2n1C]

4. The method of claim 1, wherein the composition comprises

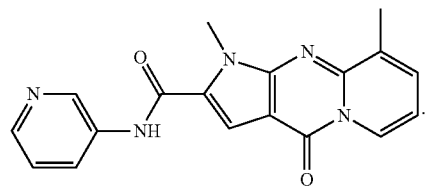 [SMILES: Cc1cccn2c(=O)c3cc(C(=O)Nc4cccnc4)n(C)c3nc12]

5. The method of claim 1, wherein the composition comprises

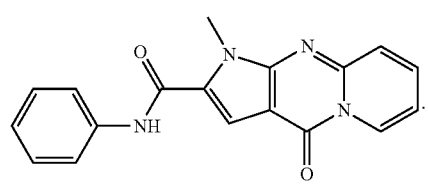 [SMILES: Cn1c(C(=O)Nc2ccccc2)cc2c(=O)n3ccccc3nc21]

6. The method of claim 1, wherein $R_3$ is an alkyl group.

* * * * *